United States Patent
Lan et al.

(10) Patent No.: US 11,890,392 B2
(45) Date of Patent: Feb. 6, 2024

(54) ABSORBABLE BONE WAX AND PREPARATION METHOD THEREOF

(71) Applicant: GUANGZHOU BEOGENE BIOTECHNOLOGY CO., LTD., Guangdong (CN)

(72) Inventors: Yong Lan, Guangdong (CN); Yu Liu, Guangdong (CN); Yu Chen, Guangdong (CN)

(73) Assignee: GUANGZHOU BEOGENE BIOTECHNOLOGY CO., LTD., Guangzhou (CN)

( * ) Notice: Subject to any disclaimer, the term of this patent is extended or adjusted under 35 U.S.C. 154(b) by 545 days.

(21) Appl. No.: 17/267,024

(22) PCT Filed: Dec. 20, 2019

(86) PCT No.: PCT/CN2019/127054
§ 371 (c)(1),
(2) Date: Feb. 9, 2021

(87) PCT Pub. No.: WO2021/027219
PCT Pub. Date: Feb. 18, 2021

(65) Prior Publication Data
US 2021/0393848 A1  Dec. 23, 2021

(30) Foreign Application Priority Data
Aug. 15, 2019  (CN) ......................... 201910757496.X

(51) Int. Cl.
A61L 24/00 (2006.01)
A61L 24/02 (2006.01)
A61L 24/06 (2006.01)
C08L 87/00 (2006.01)
C08L 3/02 (2006.01)

(52) U.S. Cl.
CPC ....... *A61L 24/0042* (2013.01); *A61L 24/0015* (2013.01); *A61L 24/02* (2013.01); *A61L 24/06* (2013.01); *C08L 3/02* (2013.01); *C08L 87/005* (2013.01); *A61L 2300/104* (2013.01); *A61L 2300/204* (2013.01); *A61L 2400/04* (2013.01); *A61L 2430/02* (2013.01)

(58) Field of Classification Search
CPC .................................................. A62L 2400/12
See application file for complete search history.

(56) References Cited

FOREIGN PATENT DOCUMENTS

| CN | 107583112 A | 1/2018 |
|---|---|---|
| CN | 109125791 A | 1/2019 |
| CN | 109287658 A | 2/2019 |
| CN | 109432487 A | 3/2019 |
| CN | 109498832 A | 3/2019 |
| CN | 109550078 A | 4/2019 |

OTHER PUBLICATIONS

Yingjun Wang et al., New material science and technology Inorganic Materials Volume, Oct. 31, 2016, pp. 1335-1336, vol. 1.

*Primary Examiner* — Sarah Alawadi

(57) ABSTRACT

Disclosed is absorbable bone wax and a preparation method thereof. The preparation method comprises the steps of: 1) mixing polyoxypropylene polyoxyethylene block copolymer (PEG-PPG-PEG) and polyoxypropylene polyoxyethylene random copolymer (PEG-PPG), and stirring evenly under heating to obtain a liquid mixture; 2) under mechanical stirring and heating condition, adding hemostatic starch microspheres to the liquid mixture obtained in step 1) to obtain a uniformly-mixed liquid; and 3) adding a bone repair material to the uniformly-mixed liquid obtained in step 2), and mixing uniformly to obtain a mixed solution, then pouring the mixed solution into a mold or sub-packaged bottle, and leaving at room temperature for solidifying and shaping to give the absorbable bone wax. The absorbable bone wax of the present invention can achieve the effect of rapid hemostasis, changing the relatively single hemostasis method with traditional bone wax which only depends on physical sealing.

15 Claims, 4 Drawing Sheets

ABSORBABLE BONE WAX AND PREPARATION METHOD THEREOF

FIELD OF THE INVENTION

The present invention relates to biomedical engineering materials, in particular, to absorbable bone wax and a preparation method thereof.

BACKGROUND OF THE INVENTION

Bone hemorrhage occurs during many traumas and surgical procedures. Therefore, it is necessary to control bone hemorrhage or perform bone hemostasis. Bone wax is a kind of bone hemostatic material, and is used to control local bone hemorrhage by applying the bone wax on cutting surfaces during surgery. At present, the bone wax widely used in surgical operations is mostly prepared from beeswax by mixing beeswax with water-insoluble hydrocarbons and vegetable oils. The disadvantage of such bone wax is poor adhesion and high brittleness at room temperature. However, the widely used bone wax will cause not only chronic inflammation but also foreign body reactions, cause non-healing interstitial bacterial infection and increases a risk of bone infection, and inhibit the bone healing process due to the non-renewable nature of such bone wax. Therefore, it is not suitable for parts that require bone regeneration and/or fusion, and it cannot be used in contaminated parts. In order to overcome these shortcomings of traditional bone wax, a research on absorbable bone wax with a function of promoting bone repair is imminent.

Polyoxypropylene polyoxyethylene block copolymer (PEG-PPG-PEG) and polyoxypropylene polyoxyethylene random copolymer (PEG-PPG) are absorbable polymer materials with good hemostatic effects. They are used as raw materials for preparing bone wax and have become research hotspots because of advantages such as non-toxic, non-irritating, good biocompatibility, controllable degradation through processing and modification, easily-absorbable degradation products and low immunoantigenicity.

Hemostatic starch microspheres refer to a kind of modified starch prepared by moderately cross-linking a cross-linking agent with hydroxyl groups of the starch in the presence of an initiator. This hemostatic starch microspheres are micron-sized, and have properties of strong adsorption, certain deformability in living organism, and easy degradation. Starch microspheres also have properties of excellent biocompatibility, non-toxicity, biodegradability and non-immunogenicity, and have a wide range of raw materials and low prices.

Starch itself has a certain degree of water absorption, while the micron-sized hemostatic starch microspheres increase the contact area with water, and can quickly absorb water in the blood. In addition, the micron-sized hemostatic starch microspheres play the role of molecular sieve, so that red blood cells, thrombin, platelets, fibrin and other effective components in the blood aggregate on the surfaces of the starch microspheres to form a gel-like mixture so as to achieve the effect of rapid hemostasis. A starch microsphere hemostatic agent that has been marketed is Arista™ AH (microporous polysaccharide hemospheres) from Medafor INC, which is a powdered hemostatic agent derived from purified potato starch. The powder does not contain any animal- or human-derived ingredients and is non-biologically active particle. It has been clinically proven that the microporous polysaccharide hemospheres have fast, effective and long-lasting hemostatic effects in anterior decompression of thoracolumbar fractures, endoscopic thyroid surgery, and sternotomy.

β-Tricalcium Phosphate (β-TCP) has good biocompatibility, bioactivity and biodegradability. It is an ideal human hard tissue repair and replacement material, and has been paid close attention in the field of biomedical engineering. The main inorganic components of human and animal bones are phosphorus and calcium, while tricalcium phosphate is mainly composed of calcium and phosphorus. The composition of tricalcium phosphate is similar to the inorganic components of bone matrix and is well integrated with bone. Animal or human cells can grow, differentiate and reproduce normally on tricalcium phosphate materials. A large number of experimental studies have proved that: β-Tricalcium Phosphate (β-TCP) has no adverse response, no rejection, no acute toxicity, no carcinogenesis, no allergy to bone marrow hematopoietic function. β-Tricalcium Phosphate (β-TCP) can achieve chemical bonding with body tissues at the interface; and it has a certain solubility in living organism, can release harmless ions to the living organism, participate in metabolism of the living organism, stimulate or induce bone regeneration, promote repair of bone defect, and show biological activity.

As a special form of metallic silver, nanosilver refers to a powder composed of metallic nanosilver particles with a particle size between 1 nm and 100 nm. Due to its extremely small particles and large surface area, the nanosilver has significant surface effects, quantum size effects and quantum tunneling effects, so that the nanosilver has super activity and permeability, and its bactericidal effect is hundreds of times that of ordinary silver. As a new type of antibacterial agent, the nanosilver has powerful antibacterial and bactericidal effects and broad-spectrum antibacterial activity. It has an incomparable antibacterial effect by traditional inorganic antibacterial agents, and has no drug resistance and has high safety. Therefore, with the increasingly serious bacterial resistance of antibiotics, the research and application of nanosilver in the field of disinfection and sterilization has received more and more attention. β-TCP-PDA-Ag is a bone repair material loaded with nanosilver, which not only has the bone repair effect of β-TCP, but also has powerful antibacterial and antibacterial effects of nanosilver.

Most of existing bone wax has beeswax as the main component, and is prepared by mixing beeswax with water-insoluble hydrocarbons and vegetable oils. The disadvantage of this type of bone wax is that the bone wax has poor adhesion and high brittleness at room temperature. The most common bone wax is non-absorbable in human body. When used in surgery, this kind of bone wax will stay at the application site for a long time, which is easy to cause infection and inflammation, thereby destroying surrounding tissues and affecting bone regrowth. In addition, the application principle of this type of bone wax is relatively simple, and is a physical blocking method to block the capillary bleeding site in bone marrow; when the amount of bleeding is large, there is a possibility that bleeding cannot be blocked. In addition, there are often bone defects during trauma or surgery, which are easy to cause infection and inflammation during trauma and surgery, thereby destroying surrounding tissues and affecting bone regrowth. However, traditional bone wax cannot effectively repair the defective bone tissue.

SUMMARY OF THE INVENTION

In order to solve the above technical problems, the technical solution adopted by the present invention includes the following aspects.

In one aspect, the present invention provides a method of preparing a bone repair material comprising:

(1) preparing a dopamine solution by dissolving dopamine hydrochloride in Tris-HCl buffer;

(2) adding β-tricalcium phosphate to the dopamine solution obtained in step (1), and after stirring uniformly, centrifuging, washing and freeze-drying, obtaining β-tricalcium phosphate coated with polydopamine labeled as β-TCP-PDA; and (3) dispersing the β-TCP-PDA obtained in step (2) into Tollens' reagent, then adding glucose and polyvinylpyrrolidone thereto and stirring evenly to obtain a β-TCP bone repair material loaded with nanosilver particles which is labeled as β-TCP-PDA-Ag, and thereby obtaining the bone repair material. Preferably, the pH of the Tris-HCl buffer is 8.5.

Preferably, in step (3), a mass ratio of glucose to $AgNO_3$ in the Tollens' reagent is 0.6:1. It should be noted that a certain amount of $AgNO_3$ is dissolved in water to prepare a 0.01 g/L $AgNO_3$ solution, and 26% ammonia water is added dropwise into the $AgNO_3$ solution to make the resultant solution brown, then ammonia water is added dropwise until the resultant solution is clear and transparent, so that the above Tollens' reagent is obtained. The inventors of the present invention have found through many experiments that when the mass ratio of glucose to $AgNO_3$ in the Tollens' reagent is 0.6:1, the silver ions in the Tollens' reagent can be reduced to nanosilver to the greatest extent without causing waste of glucose.

Preferably, the β-Tricalcium Phosphate (β-TCP) in step (2) is prepared by the steps of:

dissolving a certain amount of $Ca(NO_3)_2$ in a beaker containing deionized water to form a $Ca(NO_3)_2$ solution containing Ca;

dissolving a certain amount of $(NH_4)_2HPO_4$ in another beaker containing deionized water to form a $(NH_4)_2HPO_4$ solution containing P;

adding a certain amount of SDS to the $Ca(NO_3)_2$ solution, and adding the $(NH_4)_2HPO_4$ solution dropwise to the $Ca(NO_3)_2$ solution under mechanical stirring; in the process of adding dropwise the $(NH_4)_2HPO_4$ solution, adding ammonia water to keep pH of a whole system at 10 or greater during reaction; and after dropwise addition of the $(NH_4)_2HPO_4$ solution, continuing reacting under mechanical stirring, and then letting a resultant solution stand to precipitate; then using a buchner funnel to perform suction filtration on precipitate, and alternately washing the precipitate with deionized water and absolute ethanol until filtrate is neutral, vacuum drying the precipitate washed to be neutral to obtain loose, non-caking TCP powder, and then sintering the loose, non-caking TCP powder to obtain β-tricalcium phosphate (β-TCP) powder.

Preferably, the molar ratio of $Ca(NO_3)_2$ to $(NH_4)_2HPO_4$ is 3:1. The inventors of the present invention have found through many experiments that when the molar ratio of $Ca(NO_3)_2$ to $(NH_4)_2HPO_4$ is 3:1, the TCP can be synthesized to the maximum extent without causing waste of raw materials and formation of impurities.

In another aspect, the present invention provides a method of preparing absorbable bone wax comprising:

1) mixing a certain amount of polyoxypropylene polyoxyethylene block copolymer (PEG-PPG-PEG) and a certain amount of polyoxypropylene polyoxyethylene random copolymer (PEG-PPG), and stirring evenly under heating to obtain a liquid mixture;

2) under a condition of mechanical stirring and heating, adding a certain amount of hemostatic starch microspheres to the liquid mixture obtained in step 1) to obtain a uniformly-mixed liquid; and 3) adding a bone repair material prepared above to the uniformly-mixed liquid obtained in step 2), and mixing uniformly to obtain a mixed solution, then pouring the mixed solution into a mold or sub-packaged bottle, and leaving the mold or sub-packaged bottle at room temperature for solidifying and shaping to give the absorbable bone wax.

Preferably, the molar ratio of PEG-PPG-PEG:PEG-PPG: hemostatic starch microspheres:a bone repair material is 3:7:2:0.5. The inventors of the present invention have found through many experiments that when the molar ratio of PEG-PPG-PEG:PEG-PPG:hemostatic starch microspheres: bone repair material is 3:7:2:0.5, the prepared absorbable bone wax has properties of moderate hardness, strong plasticity and easy operation. Too little hemostatic starch microspheres will weaken the hemostatic effect, and too much will make the absorbable bone wax harder and operate inconveniently. In addition, too little bone repair material will weaken the bone repair effect, and too much will make the absorbable bone wax harder, less adhesive, and operate inconveniently.

Preferably, the hemostatic starch microspheres in step 2) are prepared by the steps of:

adding purified water to a certain amount of soluble starch and mixing thoroughly to form a starch solution, adjusting pH of the starch solution with anhydrous sodium carbonate, heating and stirring the starch solution with a magnetic stirrer to gelatinize until the starch solution is transparent, thereby obtaining a gelatinized starch solution, and cooling the gelatinized starch solution for later use;

adding purified water to a certain amount of cross-linking agent and stirring and dissolving the cross-linking agent with a magnetic stirrer to obtain a cross-linking agent solution, then pouring the cross-linking agent solution into the gelatinized starch solution, and stirring evenly to obtain a prepared starch solution; and adding a certain amount of soybean oil in a three-necked flask, then adding an emulsifier Span80 thereto, heating the three-necked flask in a constant temperature water bath device until Span80 is completely dissolved, cooling the three-necked flask to 45° C., then under mechanical stirring adding the prepared starch solution slowly, and completing a reaction at 45° C. after dropwise addition of the prepared starch solution, then subjecting a reaction solution to centrifugal separation to obtain a solution with oil phase and water phase separated, removing the oil phase, and washing precipitate alternately with absolute ethanol, distilled water, and acetone, and then freeze-drying the precipitate to obtain the hemostatic starch microspheres.

Preferably, the volume ratio of the oil phase to the water phase is in a range of 0~2:0~1. More preferably, the volume ratio is 1:1.

In yet another aspect, the present invention provides absorbable bone wax, raw materials for preparing the absorbable bone wax include PEG-PPG-PEG, PEG-PPG, hemostatic starch microspheres and a bone repair material, the molar ratio of PEG-PPG-PEG:PEG-PPG:hemostatic starch microspheres:bone repair material is 3:7:2:0.5.

The advantages according to the present invention are as follows:

Firstly, in the present invention, polyoxypropylene polyoxyethylene block copolymer (PEG-PPG-PEG) and polyoxypropylene polyoxyethylene random copolymer (PEG- PPG) which have good biocompatibility are used as raw materials for preparing the absorbable bone wax, which enhances degradability in vivo of the absorbable bone wax and facilitates absorption;

Secondly, the addition of hemostatic starch microspheres can make the effective components in blood such as red blood cells, thrombin, platelets and fibrin aggregate on surfaces of the hemostatic starch microspheres to form a gel-like mixture so as to achieve the effect of rapid hemostasis; further, the absorbable bone wax added with hemostatic starch microspheres can stop bleeding quickly and shorten the time required for hemostasis compared with traditional bone wax that only relies on physical sealing; and Finally, the addition of a bone repair material provides the necessary ionic components for the bone repair process, induces bone regeneration, and promotes bone self-repair; on the other hand, the bone repair material loaded with nanosilver particles can not only play a role of bone repair, but also achieve powerful antibacterial and antibacterial effects due to the presence of nanosilver particles, thereby reducing inflammation caused by infection.

DETAILED DESCRPTION OF PREFERRED EMBODIMENTS

Figure 1:
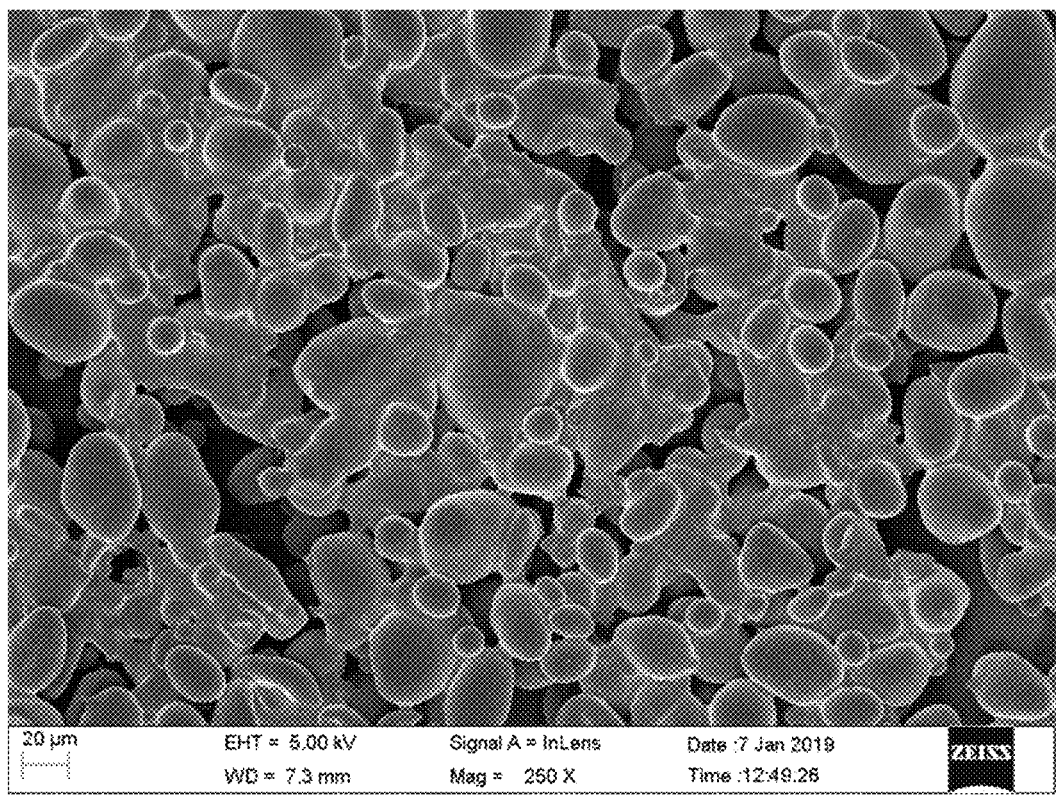
FIG. 1 is a scanning electron microscope (SEM) image of hemostatic starch microspheres.

An absorbable and degradable hemostatic material is developed in the present invention through researches of polyoxypropylene polyoxyethylene block copolymer (PEG-PPG-PEG) and polyoxypropylene polyoxyethylene random copolymer (PEG-PPG). The hemostatic starch microspheres added into the absorbable bone wax of the present invention can quickly absorb water in blood and play the role of molecular sieve, so that effective components in blood such as red blood cells, thrombin, platelets and fibrin will aggregate on surfaces of the particles to form a gel-like mixture so as to achieve a rapid hemostasis effect. In addition, the addition of a bone repair material can provide minerals needed for bone formation when repairing bone defects, effectively promote osteoblast activity and inhibit osteoblast differentiation. At the same time, the addition of nanosilver particles can effectively inhibit various gram-positive and gram-negative bacteria. Therefore, the bone repair material loaded with nanosilver particles can effectively inhibit osteomyelitis caused by various bacteria, thereby enhancing its application in clinical medicine.

The innovations and difficulties of the present invention include: 1) preparation of starch microspheres with a hemostatic function; 2) preparation of a bone repair material with an antibacterial function; and 3) organically compounding the starch microspheres with a hemostatic function and the bone repair material loaded with nanosilver particles through polyoxypropylene polyoxyethylene block copolymer (PEG-PPG-PEG) and polyoxypropylene polyoxyethylene random copolymer (PEG-PPG) to form the absorbable bone wax with hemostatic, antibacterial and bone repair functions.

In some embodiments of the present invention, the main components of bone wax are improved, which increases bioavailability and degradability of the absorbable bone wax, and reduces inflammation caused by bone wax retention; the addition of hemostatic starch microspheres can make the effective components in blood such as red blood cells, thrombin, platelets and fibrin aggregate on surfaces of the hemostatic starch microspheres to form a gel-like mixture so as to achieve the effect of rapid hemostasis; at the same time, the addition of the nanosilver-loaded bone repair material can not only effectively reduce bone tissue infection and inflammation caused by trauma and surgery, but also promote bone repair at bone defective sites caused by disease, trauma, surgery, etc.

In some embodiments, the present invention provides a method for preparing hemostatic starch microspheres, including the steps of: adding purified water to a certain amount of soluble starch and mixing thoroughly to form a starch solution, adjusting pH of the starch solution with anhydrous sodium carbonate, heating and stirring the starch solution with a magnetic stirrer to gelatinize until the starch solution is transparent, thereby obtaining a gelatinized starch solution, and cooling the gelatinized starch solution for later use; adding purified water to a certain amount of cross-linking agent and stirring and dissolving the cross-linking agent with a magnetic stirrer to obtain a cross-linking agent solution, then pouring the cross-linking agent solution into the gelatinized starch solution and stirring evenly to obtain a prepared starch solution for later use; and adding an appropriate amount of soybean oil in a three-necked flask, then adding an emulsifier Span80 thereto, heating the three-necked flask in a constant temperature water bath device at 60° C. until Span80 is completely dissolved, cooling the three-necked flask to 45° C., then under mechanical stirring adding the prepared starch solution slowly, completing a reaction at 45° C. after dropwise addition of the prepared starch solution, then subjecting a reaction solution to centrifugal separation to obtain a solution with oil phase and water phase separated, removing the oil phase and washing precipitate alternately with absolute ethanol, distilled water, and acetone, and then freeze-drying the precipitate to obtain the hemostatic starch microspheres.

The cross-linking agent in the above method can be one or more selected from a group comprising epichlorohydrin, formaldehyde, phosphorus oxychloride, sodium trimetaphosphate or tripolyphosphate, and sodium hexametaphosphate, preferably sodium trimetaphosphate. The gelatinization in the above method is performed at a temperature in a range from 40° C. to 85° C., preferably at 60° C. The adjusted pH value in the above method is 10 or greater. The above-mentioned mechanical stirring has a speed in a range from 200 r/min to 600 r/min, preferably 400 r/min. The concentration of the above-mentioned soluble starch is in a range from 2 wt % to 10 wt %, preferably 8 wt %. The volume ratio of the oil phase to the water phase in the above method is in a range of 0~2:0~1, preferably 1:1. The above-mentioned emulsifier dosage is 0.009 g/mL oil. The amount of the above-mentioned cross-linking agent (sodium trimetaphosphate) is in a range from 0.1 wt % to 1 wt % of the weight of the soluble starch. The reaction time in the above method is preferably 6 hours. The centrifugal condition mentioned above is preferably 10,000 rpm for 10 min. The freeze-drying condition in the above method is preferably −70° C. for 24 hours.

In some embodiments, the present invention provides a method for preparing β-tricalcium phosphate (β-TCP), including the steps of: weighing and dissolving a certain amount of $Ca(NO_3)_2$ in a beaker containing deionized water to form a $Ca(NO_3)_2$ solution containing Ca; then weighing and dissolving a certain amount of $(NH_4)_2HPO_4$ in another beaker containing deionized water to form a $(NH_4)_2HPO_4$ solution containing P; adding an appropriate amount of SDS to the $Ca(NO_3)_2$ solution, then adding the $(NH_4)_2HPO_4$ solution dropwise to the $Ca(NO_3)_2$ solution at a certain dropping rate under mechanical stirring; in the process of dripping the $(NH_4)_2HPO_4$ solution, adding a certain amount of ammonia water to keep pH of the whole system at 10 or greater during the reaction process; and after dropwise addition of the $(NH_4)_2HPO_4$ solution, continuing reacting for 2 hours under mechanical stirring, and then letting a resultant solution stand for one night to precipitate; then using a buchner funnel to perform suction filtration on precipitate, and alternately washing the precipitate with deionized water and absolute ethanol until the filtrate is neutral; vacuum drying the precipitate washed to be neutral to obtain loose, non-caking TCP powder, and then sintering the loose, non-caking TCP powder in a muffle furnace to obtain β-tricalcium phosphate (β-TCP) powder.

The molar ratio of $Ca(NO_3)_2$ to $(NH_4)_2HPO_4$ in the above method is preferably a 3:1. The speed of mechanical stirring in the above method is preferably in a range from 400 r/min to 600 r/min. The vacuum drying condition in the above method is preferably 110° C. for 12 hours. The sintering condition of the above middle muffle furnace is preferably 1,000° C. for 5 hours.

In some embodiments, the present invention provides a preparation method of a β-TCP-PDA-Ag bone repair material, including the steps of: weighing a certain amount of dopamine hydrochloride and dissolving it in a certain volume of Tris-HCl buffer of pH 8.5 to obtain a 2 mg/ml dopamine solution, then dispersing an appropriate amount of β-TCP prepared above according to a certain ratio into the dopamine solution, magnetically stirring the resultant solution at room temperature for 48 hours, and after centrifuging, washing, and freeze-drying, obtaining β-TCP coated with polydopamine, labeled as β-TCP-PDA; dissolving a certain amount of $AgNO_3$ in water to obtain a 0.01 g/L $AgNO_3$ solution, adding 26% ammonia solution dropwise thereto to make the $AgNO_3$ solution brown, then continuing adding dropwise until the $AgNO_3$ solution is clear and transparent, thereby obtaining Tollens' reagent; dispersing 0.4 g β-TCP-PDA into the Tollens' reagent, then adding a certain amount of glucose as a reducing agent in a certain ratio, adding polyvinylpyrrolidone to play a role in assisting dispersion after dissolution of polyvinylpyrrolidone, and magnetically stirring for 8 hours at room temperature, thereby obtaining the β-TCP bone repair material loaded with nano-silver particles, labeled as β-TCP-PDA-Ag.

The certain ratio in the above method is the molar ratio of dopamine hydrochloride to β-TCP, preferably 1:1. The speed of magnetic stirring in the above method is preferably in a range from 400 r/min to 600 r/min. The centrifugal condition in the above method is preferably 10,000 rpm for 10 min. The freeze-drying condition in the above method is preferably −70° C. for 24 hours. The certain ratio of glucose in the above method is the mass ratio of glucose to $AgNO_3$, preferably 0.6. The dissolved concentration of polyvinylpyrrolidone in the above method is 5 wt %.

In some embodiments, the present invention provides a method for preparing absorbable bone wax that has hemostatic and anti-inflammatory effects and can promote bone repair, including the steps of: mixing an appropriate amount of polyoxypropylene polyoxyethylene block copolymer (PEG-PPG-PEG) and an appropriate amount of polyoxypropylene polyoxyethylene random copolymer (PEG-PPG), and heating the mixture under the condition of mechanical stirring to make the mixture appear liquid and mix uniformly; under the condition of mechanical stirring and heating, slowly adding a certain amount of hemostatic starch microspheres to the above-mentioned uniformly-mixed liquid mixture and stirring and mixing uniformly, then adding a certain amount of the corresponding bone repair material to the above-mentioned uniformly-mixed liquid and mixing uniformly; and pouring the resultant uniformly-mixed liquid mixture into a pre-prepared mold or sub-packaging bottle, and placing the mold or sub-packaging bottle at room temperature for 2 hours to solidify and shape.

The preferred molecular weight of the polyoxypropylene polyoxyethylene block copolymer (PEG-PPG-PEG) mentioned above is in a range from 4,400 to 14,600. The preferred range of the molecular weight of the above-mentioned polyoxypropylene polyoxyethylene random copolymer (PEG-PPG) is 2,500 to 12,000. The ratio of PEG-PPG-PEG:PEG-PPG:hemostatic starch microspheres:a bone repair material is preferably 3:7:2:0.5, and the ratio is a molar ratio. The speed of mechanical stirring in the above method is preferably in a range from 400 r/min to 600 r/min. The heating temperature in the above method is preferably in a range from 60° C. to 100° C.

In some embodiments, the present invention provides absorbable bone wax that has dual hemostatic effects and promotes bone repair and a preparation method thereof. The absorbable bone wax has good biocompatibility and degradability, can provide good physiological conditions for absorption and degradation in vivo, and has the same principle of hemostatic properties as traditional bone wax. The addition of hemostatic starch microspheres can make the effective components in the blood such as red blood cells, thrombin, platelets and fibrin aggregate on the surfaces of the hemostatic starch microspheres to form a gel-like mixture so as to achieve the effect of rapid hemostasis. The absorbable bone wax added with hemostatic starch microspheres can stop bleeding quickly and shorten the time required for hemostasis compared to traditional bone wax that only relies on physical sealing to stop bleeding. In addition, the addition of bone repair materials provides ionic components needed for the bone repair process, induces bone regeneration, and promotes bone self-repair.

Furthermore, β-tricalcium phosphate (β-TCP) has no adverse response, no rejection, no acute toxicity, no carcinogenesis, and no allergy to bone marrow hematopoietic function. β-Tricalcium Phosphate (β-TCP) can achieve chemical bonding with body tissues at the interface, and it has a certain solubility in living organism, can release harmless ions to the living organism, participate in metabolism of the living organism, stimulate or induce bone regeneration, promote repair of bone defect, and show biological activity. As a new type of antibacterial agent, nanosilver has powerful antibacterial and bactericidal effect and broad-spectrum antibacterial activity, and has an incomparable antibacterial effect by traditional inorganic antibacterial agents; in addition, nanosilver has no drug resistance, and has high safety. β-TCP-PDA-Ag is a bone repair material loaded with nanosilver, which not only has the bone repair effect of β-TCP, but also has the powerful antibacterial and antibacterial effect of nanosilver.

The preparation method of the above-mentioned absorbable bone wax include the following steps: 1) preparing a hemostatic starch microsphere material; 2) preparing a bone repair material; 3) preparing silver-loaded bone repair material; and 4) preparing absorbable bone wax that can promote bone repair and has double hemostatic effects. The absorbable bone wax of the present invention is simple to prepare and use, and the required raw materials are easily available, so that the absorbable bone wax is expected to be widely used in the field of biomedical engineering materials.

In order to better illustrate the purposes, technical solutions and advantages of the present invention, the present invention will be further described below with reference to the drawings and specific embodiments. Unless otherwise specified, the experimental methods or test methods in the present invention are conventional methods.

Example 1: Preparation of Hemostatic Starch Microspheres 24 g of soluble starch was weighted and dissolved completely in an appropriate amount of purified water to form a 8 wt % starch solution, the pH of which was adjusted to 10 or greater with anhydrous sodium carbonate, and the starch solution was heated to 60° C. on a magnetic stirrer and stired at a speed of 400 r/min to gelatinize until the starch solution was transparent, then the gelatinized starch solution was cooled for later use. 2.4 g of cross-linking agent was weighted and added into another beaker containing an appropriate amount of purified water, the cross-linking agent was stirred by a magnetic stirrer and dissolved in the purified water to give a cross-linking agent solution, and then the cross-linking agent solution was poured into the gelatinized starch solution and stirred evenly to obtain a prepared starch solution. According to the water/oil ratio of ½, 600 ml of soybean oil and 5.4 g of emulsifier Span80 were added into a three-necked flask, and the three-necked flask was put in a constant temperature water bath and heated to 60° C. to completely dissolve Span80, then cooled to 45° C.; and under mechanical stirring, the prepared starch solution was slowly added into the three-necked flask; after the prepared starch solution was added dropwise, the mixture in the three-necked flask was reacted for a period of time at 45° C.; after centrifugal separation, the oil phase was removed, and the obtained precipitate was washed alternately with absolute ethanol, distilled water, and acetone, and then freeze-dried to obtain hemostatic starch microspheres.

FIG. 1 is a scanning electron microscope (SEM) image of the hemostatic starch microspheres. It could be clearly seen from FIG. 1 that the prepared hemostatic starch microspheres have a spherical structure. The diameters of the balls are less than 100 μm, and the balls are spherical particles in the micron range, so that the hemostatic starch prepared is starch microspheres.

Example 2: Preparation of a β-Tricalcium Phosphate (β-TCP) Bone Repair Material A certain amount of $Ca(NO_3)_2$ was weighted and dissolved in a beaker containing deionized water to prepare a 0.5 mol/L $Ca(NO_3)_2$ solution, and a certain amount of $(NH_4)_2HPO_4$ was weighted and dissolved in another beaker containing deionized water to prepare a 0.5 mol/L $(NH_4)_2HPO_4$ solution. An appropriate amount of SDS was added to the $Ca(NO_3)_2$ solution, and under mechanical stirring with a speed in a range from 400 rpm to 600 rpm, the $(NH_4)_2HPO_4$ solution was added dropwise to the $Ca(NO_3)_2$ solution according to the molar ratio of $Ca(NO_3)_2$ to $(NH_4)_2HPO_4$ of 3:1. In the process of dripping the $(NH_4)_2HPO_4$ solution, a certain amount of ammonia water was added to keep the pH of the whole system at 10 or greater during the reaction process. After the $(NH_4)_2HPO_4$ solution was added dropwise, the mixture was reacted for 2 hours under mechanical stirring, and the mixture was left for one night. A Buchner funnel was used to perform suction filtration on the mixture, and the precipitate was alternately washed with deionized water and absolute ethanol until the filtrate was neutral. Then the precipitate washed to be neutral was vacuum dried at 110° C. for 12 hours to obtain loose, non-caking TCP powder. The obtained loose, non-caking TCP powder was placed in a muffle furnace at 1000° C. and sintered for 5 hours to obtain β-tricalcium phosphate (β-TCP) powder.

Example 3: Preparation of a β-TCP-PDA-Ag Bone Repair Material

A certain amount of dopamine hydrochloride was weighted and dissolved in a certain volume of Tris-HCl buffer with pH 8.5 to prepare a 2 mg/ml dopamine solution; according to the ratio of dopamine hydrochloride to β-TCP of 1:1, an appropriate amount of β-TCP prepared in Example 2 was dispersed into the dopamine solution; and after magnetically stirred at room temperature for 48 hours, the mixed solution was centrifuged, washed, and freeze-dried to obtain β-TCP coated with polydopamine, labeled as β-TCP-PDA.

A certain quality of $AgNO_3$ was dissolved in water to prepare a 0.01 g/L $AgNO_3$ solution, then 26% ammonia solution was dropwise added to make the $AgNO_3$ solution brown. The 26% ammonia solution was continually added dropwise until the $AgNO_3$ solution was clear and transparent, thereby obtaining Tollens' reagent. 0.4 g of β-TCP-PDA was dispersed into the Tollens' reagent, then a certain amount of glucose was added as a reducing agent according to the ratio of glucose:$AgNO_3$ of 0.6:1, and 5 wt % polyvinylpyrrolidone was added to help dispersion after dissolution. Then the resultant mixture was magnetically stirred at a speed in a range from 400 r/min to 600 r/min at room temperature for 8 hours, and the β-TCP bone repair material loaded with nanosilver particles was obtained, labeled as β-TCP-PDA-Ag.

Example 4: Preparation of Absorbable Bone Wax that has Hemostatic and Anti-Inflammatory Effects and Promotes Bone Repair An appropriate amount of polyoxypropylene polyoxyethylene block copolymer (PEG-PPG-PEG) and an appropriate amount of polyoxypropylene polyoxyethylene random copolymer (PEG-PPG) were mixed, and heated under the condition of mechanical stirring to make the mixture appear liquid and mix evenly. Under the condition of mechanical stirring and heating, a certain amount of hemostatic starch microspheres (prepared in Example 1) was slowly added to the above-mentioned evenly-mixed liquid mixture, and stirred and mixed evenly. Then, a certain amount of the corresponding bone repair material (prepared in Example 3) was added into the above mixed liquid, and mixed evenly. The resultant evenly-mixed mixture was poured into a pre-prepared mold or sub-packaged bottle, and the mold or sub-packaged bottle was left at room temperature for 2 hours to solidify and shape so as to form the absorbable bone wax.

Preferably, the molecular weight of polyoxypropylene polyoxyethylene block copolymer (PEG-PPG-PEG) is in a range from 4,400 to 14,600; the molecular weight of polyoxypropylene polyoxyethylene random copolymer (PEG-PPG) is in a range from 2,500 to 12,000; the molar ratio of PEG-PPG-PEG:PEG-PPG:hemostatic starch microspheres:bone repair material is 3:7:2:0.5; the speed of mechanical stirring is in a range from 400 r/min to 600 r/min; and the heating temperature is in a range from 60° C. to 100° C.

Example 5: Identification of Bone Repair Materials in Each Example

Figure 2:
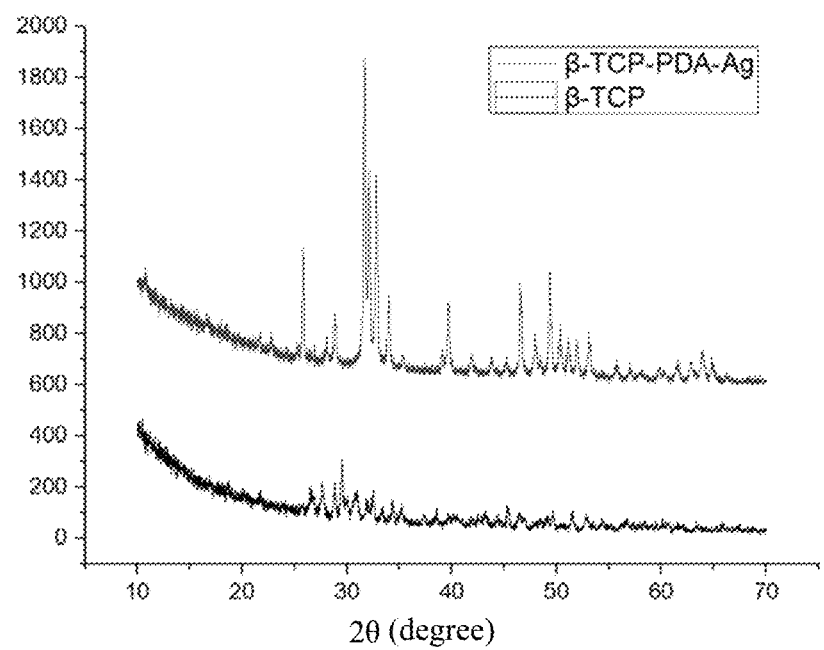
FIG. 2 is a RD (XRD) diagram of β-TCP and β-TCP-PDA-Ag; in which the horizontal axis represents an angle.

The bone repair materials prepared in Example 2 and Example 3 were characterized by X-ray diffraction, and the results obtained were shown in FIG. 2. It can be seen from FIG. 2 that compared β-TCP with β-TCP-PDA-Ag, the addition of nanosilver does not change the structure of β-TCP; in the X-RD pattern of β-TCP, there are characteristic peaks at 28°, 31°, and 34°, which corresponds to the standard X-RD pattern of β-TCP; while in the pattern of β-TCP-PDA-Ag, there are 5 characteristic peaks between 35° and 85°, which corresponds to characteristic peaks of nanosilver. Therefore, it can be proved from FIG. 2 that the prepared materials are β-TCP and β-TCP-PDA-Ag, and the addition of nanosilver does not change the structure of β-TCP.

Example 6: Hemostatic Effect of Absorbable Bone Wax in Each Example

Figure 6A:
FIG. 6A is a diagram showing hemostatic effect in vivo of absorbable bone wax.
Figure 6B:
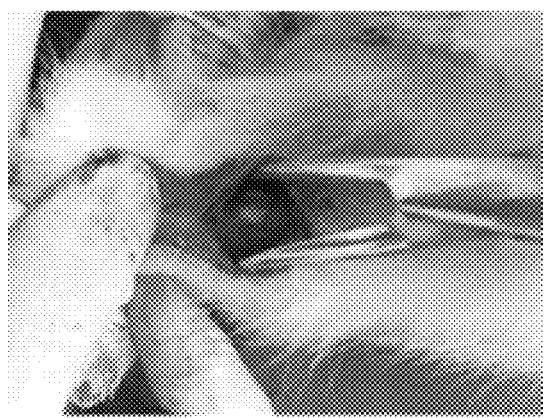
FIG. 6B is a diagram showing hemostatic effect in vivo of β-TCP/hemostatic starch microspheres/absorbable bone wax.
Figure 6C:
FIG. 6C is a diagram showing hemostatic effect in vivo of β-TCP-PDA-Ag/hemostatic starch microspheres/absorbable bone wax.

A, B, and C in Table 1 and Table 2 respectively represent: absorbable bone wax, β-TCP/hemostatic starch microspheres/absorbable bone wax, and β-TCP-PDA-Ag/hemostatic starch microspheres/absorbable bone wax. From FIGS. 6A-6C, it could be clearly seen that each absorbable bone wax has a good hemostatic effect; and from Table 1 and Table 2, it could be seen that the hemostatic effects of B and C are better than that of A, while the difference in hemostatic effect between B and C is almost negligible, which shows that the absorbable bone wax added with hemostatic starch microspheres has better hemostasis effect.

TABLE 1 coagulation parameters of different absorbable bone wax

| Sample | R (min) | K (min) | α (deg) | MA (mm) |
|---|---|---|---|---|
| Normal range | 5~10 | 1~3 | 53~72 | 50~70 |
| A | 6.1 | 2.2 | 53.5 | 55.7 |
| B | 5.5 | 2.7 | 61.4 | 56.7 |
| C | 5.2 | 2.5 | 65.7 | 52.3 |

TABLE 2 hemostatic times of different absorbable bone wax

| Sample | A | B | C |
|---|---|---|---|
| Hemostatic time (s) | 8.0 | 5.9 | 5.1 |

Example 7: APPT/PT of Absorbable Bone Wax that has Hemostatic and Anti-Inflammatory Effects and Promotes Bone Repair Activated partial thromboplastin time (hereinafter referred to as APTT), prothrombin time (hereinafter referred to as PT) and fibrinogen time (hereinafter referred to as FT) of a mixture of plasma and the absorbable bone wax that has hemostatic and anti-inflammatory effects and promotes bone repair were measured by a whole blood analyzer. The anticoagulated healthy blood was centrifuged at 1000×g for 10 min, and the supernatant was collected. 180 μL of plasma was mixed uniformly with 20 μL of PBS or extract of absorbable bone wax that has hemostatic and anti-inflammatory effects and promots bone repair, then the corresponding reagents were added at 37° C., and the resulting mixture was analyzed by a coagulometer. The test was performed 3 times in parallel.

Figure 5:
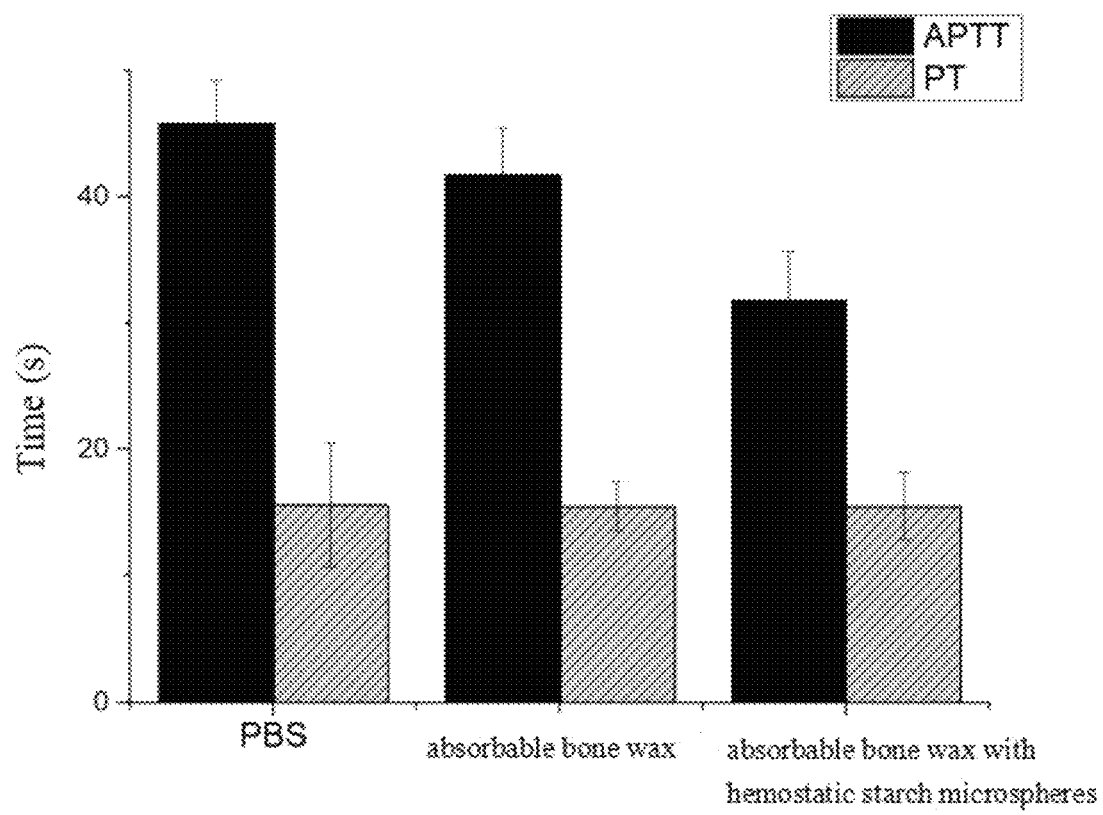
FIG. 5 is a diagram showing test results of APTT and PT of absorbable bone wax that has hemostatic and anti-inflammatory effects and promotes bone repair.

The results are shown in FIG. 5. It can be seen from FIG. 5 that the APTT value of absorbable bone wax is significantly lower than that of PBS; and the APTT of absorbable bone wax with hemostatic starch microspheres is significantly reduced compared with the absorbable bone wax without hemostatic starch microspheres and PBS. From FIG. 5, it can be seen that the PT values are not be changed obviously, which indicates that both absorbable bone wax and hemostatic starch microspheres could effectively promote blood coagulation.

Example 8: Cell Activity Test of Absorbable Bone Wax that has Hemostatic and Anti-Inflammatory Effects and Promotes Bone Repair Cell viability of the absorbable bone wax that has hemostatic and anti-inflammatory effects and promotes bone repair was detected by the CCK-8 method. The cells used in this experiment were 3T3 cells, and the culture medium used for cultivating the cells was the DMEM culture medium containing 10% fetal bovine serum and 1% dual antibody (a mixed solution of penicillin and streptomycin). The cultivation is performed in an incubator at a temperature of 37° C. with a $CO_2$ concentration of 5%. In the process of cultivation, the cell culture medium should be changed every two days. The purpose of changing the cell culture medium is to provide new nutrients for the cells and remove non-adherent cells and cell metabolites. The sterilized absorbable bone waxes that has hemostatic and anti-inflammatory effects and promotes bone repair in different examples were placed in a 48-well plate, then 50 μL of treated cell suspension was added dropwise onto the absorbable bone wax. After incubation in the incubator for 2 hours, 450 μL of culture solution was added onto each group of stents for further cultivation. The CCK-8 reagent was added in a ratio of 1:10 after 1, 4, 7 and 10 days of cultivation for further cultivation for 2 to 4 hours, which meant that 10 μL of CCK-8 reagents are added to 100 μL of culture solution. At 450 nm wavelength, a microplate reader was used to read the absorbance value of each well.

Figure 3:
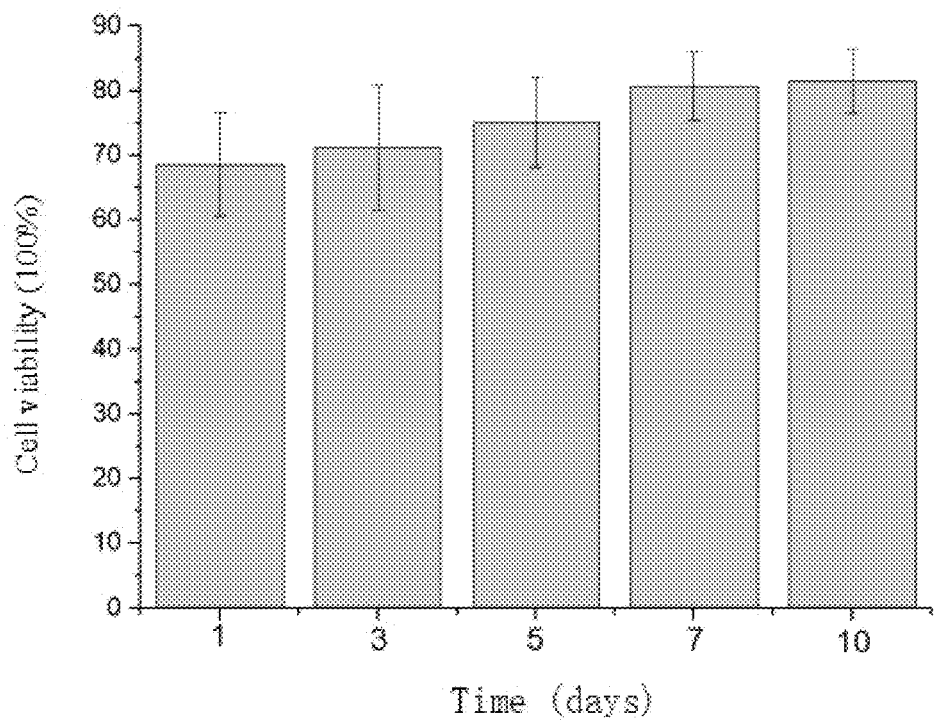
FIG. 3 is a diagram showing cell viability of absorbable bone wax that has hemostatic and anti-inflammatory effects and promotes bone repair.

The result is shown in FIG. 3. It can be seen from FIG. 3 that the absorbable bone wax that has hemostatic and anti-inflammatory effects and promotes bone repair in experimental groups and the control group show obvious cell proliferation on the 4th, 7th, and 10th days compared with the first day. Thus, the absorbable bone wax that has hemostatic and anti-inflammatory effects and promotes bone repair has good biocompatibility.

Example 9: Alkaline Phosphatase (ALP) Activity Detection of Absorbable Bone Wax that has Hemostatic and Anti-Inflammatory Effects and Promotes Bone Repair The sterilized absorbable bone wax that has hemostatic and anti-inflammatory effects and promotes bone repair of different groups was placed in a 48-well culture plate. The cells cultured to the third generation were digested and separated from a culture flask with 0.25% trypsin and centrifuged at 1,000 rpm for 5 minutes, and the supernatant was discarded, then α-DMEM culture medium containing serum and dual antibody (a mixed solution of penicillin and streptomycin) was added into the cells, and the cell concentration was adjusted to $5\times10^7$ cells per milliliter. Each absorbable bone wax sample that has hemostatic and anti-inflammatory effects and promotes bone repair was inoculated with 20 µL of the above cell suspension, and cultivated in an incubator having 5% $CO_2$ at 37° C. for 2 hours, and then 500 µL of culture medium was added for further cultivation for 7 days and 14 days. During the cultivation period, the culture medium was changed every 2 to 3 days to provide sufficient nutrients for the cells. The absorbable bone wax that has hemostatic, anti-inflammatory and promotes bone repair was taken out from the 48-well plate, rinsed with sterile PBS solution 3 times, and then 500 µL of culture medium was added to therein. Subsequently, the resultant mixture was placed in an ultrasonic cell disruptor at a temperature of 4° C. for cell disruption. The disrupted cells were centrifuged, and the supernatant was collected. 500 µL of the ALP substrate reaction solution was added to the supernatant to react for 30 min in the water bath at a temperature of 37° C. In order to stop the reaction, 500 µL of 0.1 M NaOH was added to the reaction solution, then a UV-visible spectrometer was used to measure the spectrophotometric values of the samples at 405 nm, and the ALP was calculated with the help of the instructions. The absorbable bone wax that has hemostatic and anti-inflammatory effects and promotes bone repair of each group at each time point was tested in parallel at least 3 times.

Figure 4:
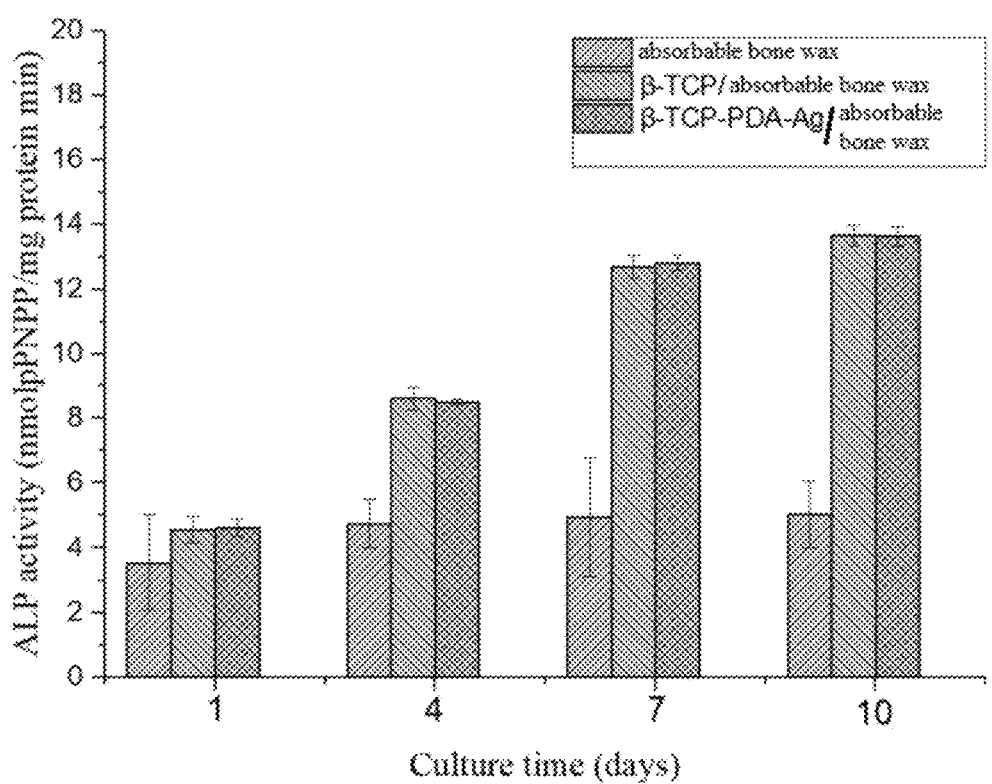
FIG. 4 is a diagram showing alkaline phosphatase (ALP) activity of absorbable bone wax that has hemostatic and anti-inflammatory effects and promotes bone repair.

The experimental results are shown in FIG. 4. It can be seen from FIG. 4 that the ALP activity of the cells added with the absorbable bone wax that has hemostatic, anti-inflammatory effects and promotes bone repair in each experimental group shows an increasing trend with the extension of the incubation time. Therefore, the experimental results show that the absorbable bone wax added with a bone repair material is beneficial to osteogenic differentiation.

Example 10: Antibacterial Performance Test of Absorbable Bone Wax that has Hemostatic and Anti-Inflammatory Effects and Promotes Bone Repair The absorbable bone wax and the absorbable bone wax loaded with β-TCP-PDA-Ag were placed on solid medium coated with *Staphylococcus aureus*, and left overnight at 37° C., then an antibacterial ring experiment was conducted to observe the antibacterial effects of absorbable bone wax and absorbable bone wax loaded with β-TCP-PDA-Ag.

Figure 7:
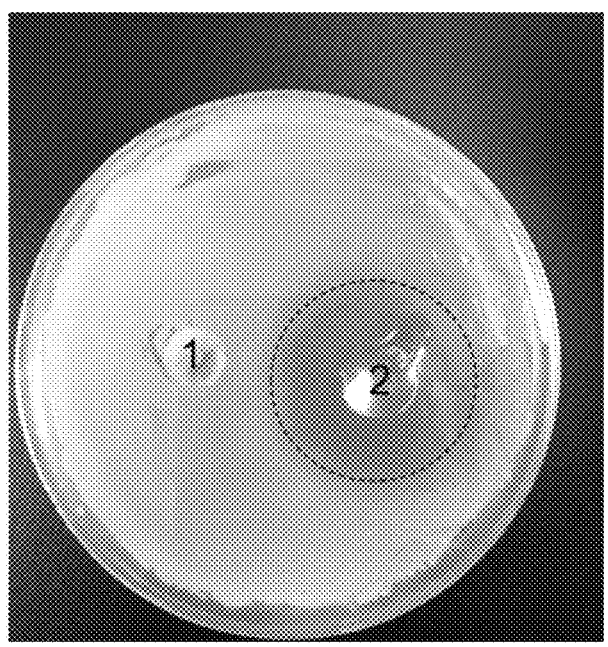
FIG. 7 is a diagram showing the test result of antibacterial performance of absorbable bone wax (1) and absorbable bone wax that has hemostatic and anti-inflammatory effects and promotes bone repair (2).

The results are shown in FIGS. 5 and 7. In FIG. 7, "1" represents the absorbable bone wax in FIG. 5, and "2" represents the absorbable bone wax loaded with β-TCP-PDA-Ag in FIG. 5. It could be clearly seen from FIG. 7 that the absorbable bone wax loaded with β-TCP-PDA-Ag has a good antibacterial effect, and the absorbable bone wax has no antibacterial effect.

Finally, it should be noted that the above embodiments are only used to illustrate the technical solutions of the present invention and not to limit the protection scope of the present invention. Although the present invention has been described in detail with reference to preferred embodiments, those skilled in the art should understand that, modifications or equivalent replacements could be made to the technical solutions of the present invention without departing from the spirit and scope of the technical solution of the present invention.

What is claimed is:

1. A method of preparing a bone repair material, comprising:
   (1) preparing a dopamine solution by dissolving dopamine hydrochloride in Tris-HCl buffer;
   (2) adding β-tricalcium phosphate to the dopamine solution obtained in step (1), and after stirring uniformly, centrifuging, washing and freeze-drying, obtaining β-tricalcium phosphate coated with polydopamine labeled as β-TCP-PDA; and
   (3) dispersing the β-TCP-PDA obtained in step (2) into Tollens' reagent, then adding glucose and polyvinylpyrrolidone thereto and stirring evenly to obtain a β-TCP bone repair material loaded with nanosilver particles which is labeled as β-TCP-PDA-Ag, and thereby obtaining the bone repair material.

2. The method of claim 1, wherein in step (3), a mass ratio of glucose to $AgNO_3$ in the Tollens' reagent is 0.6:1.

3. The method of claim 1, wherein the β-Tricalcium Phosphate (β-TCP) in step (2) is prepared by the steps of:
   dissolving a certain amount of $Ca(NO_3)_2$ in a beaker containing deionized water to form a $Ca(NO_3)_2$ solution containing Ca;
   dissolving a certain amount of $(NH_4)_2HPO_4$ in another beaker containing deionized water to form a $(NH_4)_2HPO_4$ solution containing P;
   adding a certain amount of SDS to the $Ca(NO_3)_2$ solution, and adding the $(NH_4)_2HPO_4$ solution dropwise to the $Ca(NO_3)_2$ solution under mechanical stirring; in the process of adding dropwise the $(NH_4)_2HPO_4$ solution, adding ammonia water to keep pH of a whole system at 10 or greater during reaction; and
   after dropwise addition of the $(NH_4)_2HPO_4$ solution, continuing reacting under mechanical stirring, and letting a resultant solution stand to precipitate; then using a buchner funnel to perform suction filtration on precipitate, and alternately washing the precipitate with deionized water and absolute ethanol until filtrate is neutral, vacuum drying the precipitate washed to be neutral to obtain loose, non-caking TCP powder, and then sintering the loose, non-caking TCP powder to obtain β-tricalcium phosphate (β-TCP) powder.

4. The method of claim 3, wherein a molar ratio of $Ca(NO_3)_2:(NH_4)_2HPO_4$ is 3:1.

5. A method of preparing absorbable bone wax, comprising:
1) mixing a certain amount of polyoxypropylene polyoxyethylene block copolymer (PEG-PPG-PEG) and a certain amount of polyoxypropylene polyoxyethylene random copolymer (PEG-PPG), and stirring evenly under heating to obtain a liquid mixture;
2) under a condition of mechanical stirring and heating, adding a certain amount of hemostatic starch microspheres to the liquid mixture obtained in step 1) to obtain a uniformly-mixed liquid; and
3) adding a bone repair material prepared in claim 1 to the uniformly-mixed liquid obtained in step 2) and mixing uniformly to obtain a mixed solution, then pouring the mixed solution into a mold or sub-packaged bottle, and leaving the mold or sub-packaged bottle at room temperature for solidifying and shaping to give the absorbable bone wax.

6. The method of claim 5, wherein a molar ratio of PEG-PPG-PEG:PEG-PPG:hemostatic starch microspheres:a bone repair material is 3:7:2:0.5.

7. The method of claim 5, wherein the hemostatic starch microspheres in step 2) are prepared by the steps of: adding purified water to a certain amount of soluble starch and mixing thoroughly to form a starch solution, adjusting pH of the starch solution with anhydrous sodium carbonate, heating and stirring the starch solution with a magnetic stirrer to gelatinize until the starch solution is transparent, thereby obtaining a gelatinized starch solution, and cooling the gelatinized starch solution for later use; adding purified water to a certain amount of cross-linking agent and stirring and dissolving the cross-linking agent with a magnetic stirrer to obtain a cross-linking agent solution, then pouring the cross-linking agent solution into the gelatinized starch solution and stirring evenly to obtain a prepared starch solution; and adding a certain amount of soybean oil in a three-necked flask, then adding an emulsifier thereto, heating the three-necked flask in a constant temperature water bath device until the emulsifier is completely dissolved, cooling the three-necked flask to 45° C., then under mechanical stirring adding the prepared starch solution slowly, completing a reaction at 45° C. after dropwise addition of the prepared starch solution, then subjecting a reaction solution to centrifugal separation to obtain a solution with oil phase and water phase separated, removing the oil phase, and washing precipitate alternately with absolute ethanol, distilled water, and acetone, and then freeze-drying the precipitate to obtain the hemostatic starch microspheres.

8. The method of claim 7, wherein a volume ratio of the oil phase to the water phase is in a range of 0~2:0~1.

9. The method of claim 8, wherein the volume ratio is 1:1.

10. An absorbable bone wax, wherein raw materials for preparing the absorbable bone wax include PEG-PPG-PEG, PEG-PPG, hemostatic starch microspheres and a bone repair material, and a molar ratio of PEG-PPG-PEG:PEG-PPG:hemostatic starch microspheres:a bone repair material is 3:7:2:0.5.

11. A method of preparing absorbable bone wax, comprising:
1) mixing a certain amount of polyoxypropylene polyoxyethylene block copolymer (PEG-PPG-PEG) and a certain amount of polyoxypropylene polyoxyethylene random copolymer (PEG-PPG), and stirring evenly under heating to obtain a liquid mixture;
2) under a condition of mechanical stirring and heating, adding a certain amount of hemostatic starch microspheres to the liquid mixture obtained in step 1) to obtain a uniformly-mixed liquid; and
3) adding a bone repair material prepared in claim 2 to the uniformly-mixed liquid obtained in step 2) and mixing uniformly to obtain a mixed solution, then pouring the mixed solution into a mold or sub-packaged bottle, and leaving the mold or sub-packaged bottle at room temperature for solidifying and shaping to give the absorbable bone wax.

12. The method of claim 11, wherein a molar ratio of PEG-PPG-PEG:PEG-PPG:hemostatic starch microspheres:a bone repair material is 3:7:2:0.5.

13. The method of claim 11, wherein the hemostatic starch microspheres in step 2) are prepared by the steps of: adding purified water to a certain amount of soluble starch and mixing thoroughly to form a starch solution, adjusting pH of the starch solution with anhydrous sodium carbonate, heating and stirring the starch solution with a magnetic stirrer to gelatinize until the starch solution is transparent, thereby obtaining a gelatinized starch solution, and cooling the gelatinized starch solution for later use; adding purified water to a certain amount of cross-linking agent and stirring and dissolving the cross-linking agent with a magnetic stirrer to obtain a cross-linking agent solution, then pouring the cross-linking agent solution into the gelatinized starch solution and stirring evenly to obtain a prepared starch solution; and adding a certain amount of soybean oil in a three-necked flask, then adding an emulsifier thereto, heating the three-necked flask in a constant temperature water bath device until the emulsifier is completely dissolved, cooling the three-necked flask to 45° C., then under mechanical stirring adding the prepared starch solution slowly, completing a reaction at 45° C. after dropwise addition of the prepared starch solution, then subjecting a reaction solution to centrifugal separation to obtain a solution with oil phase and water phase separated, removing the oil phase, and washing precipitate alternately with absolute ethanol, distilled water, and acetone, and then freeze-drying the precipitate to obtain the hemostatic starch microspheres.

14. The method of claim 13, wherein a volume ratio of the oil phase to the water phase is in a range of 0~2:0~1.

15. The method of claim 14, wherein the volume ratio is 1:1.

* * * * *